US012788968B2

(12) United States Patent
Zhu et al.

(10) Patent No.: US 12,788,968 B2
(45) Date of Patent: Nov. 10, 2026

(54) IMPLANTABLE MEDICAL LEAD

(71) Applicant: SCENERAY CO., LTD., Suzhou (CN)

(72) Inventors: Weiran Zhu, Suzhou (CN); Chuanjiang Jiang, Suzhou (CN); Mingkun Zhang, Suzhou (CN)

(73) Assignee: SCENERAY CO., LTD., Suzhou (CN)

( * ) Notice: Subject to any disclaimer, the term of this patent is extended or adjusted under 35 U.S.C. 154(b) by 225 days.

(21) Appl. No.: 18/692,753

(22) PCT Filed: Aug. 8, 2022

(86) PCT No.: PCT/CN2022/110914
§ 371 (c)(1),
(2) Date: Mar. 15, 2024

(87) PCT Pub. No.: WO2023/040509
PCT Pub. Date: Mar. 23, 2023

(65) Prior Publication Data

US 2024/0374890 A1 Nov. 14, 2024

(30) Foreign Application Priority Data

Sep. 17, 2021 (CN) ........................ 202111093647.X

(51) Int. Cl.
*A61N 1/05* (2006.01)

(52) U.S. Cl.
CPC .................................... *A61N 1/05* (2013.01)

(58) Field of Classification Search
CPC ... A61N 1/05; A61N 1/04; A61N 1/36; A61N 1/0529; A61N 1/3605; A61N 1/36125; A61B 5/293
See application file for complete search history.

(56) References Cited

U.S. PATENT DOCUMENTS 10,589,085 B2 * 3/2020 Young .................. A61N 1/3605
2010/0256694 A1 10/2010 Barker
(Continued)

FOREIGN PATENT DOCUMENTS

CN 103446665 A 12/2013
CN 107297023 A 10/2017
(Continued)

OTHER PUBLICATIONS

International Search Report dated Oct. 11, 2022, for International Application No. PCT/CN2022/110914 and translation (6 pgs).
(Continued)

*Primary Examiner* — Paula J Stice
(74) *Attorney, Agent, or Firm* — ArentFox Schiff LLP; Joseph M. Maraia

(57) ABSTRACT

An implantable medical lead comprises a conductive flexible circuit board, wherein the conductive flexible circuit board is divided into a stimulation segment, an intermediate segment and a connection segment; an outer surface of the stimulation segment of the conductive flexible circuit board is provided with a plurality of stimulation contacts, and an outer surface of the connection segment of the conductive flexible circuit board is provided with a plurality of first connection contacts; the outer surface of the stimulation segment of the conductive flexible circuit board is provided with collection contacts, the conductive flexible circuit board is provided with second connection contacts, a plurality of collection contact conductive layers are embedded in the conductive flexible circuit board, and the second connection contacts are electrically connected to the collection contacts through the collection contact conductive layers. The implantable medical lead accurately detects data of an electric field around the stimulation contacts.

16 Claims, 5 Drawing Sheets

(56) References Cited

U.S. PATENT DOCUMENTS

| | | | | |
|---|---|---|---|---|
| 2010/0331938 | A1 | 12/2010 | Sommer et al. | |
| 2013/0085361 | A1* | 4/2013 | Mercanzini .......... | A61B 5/4041 600/377 |
| 2017/0028191 | A1* | 2/2017 | Mercanzini .............. | A61B 5/24 |
| 2018/0169405 | A1 | 6/2018 | Kent et al. | |
| 2020/0215335 | A1* | 7/2020 | McLaughlin ............ | A61N 1/05 |

FOREIGN PATENT DOCUMENTS

| | | | |
|---|---|---|---|
| CN | 208436256 | U | 1/2019 |
| CN | 209137753 | U | 7/2019 |
| CN | 111330157 | A | 6/2020 |
| CN | 111744107 | A | 10/2020 |
| CN | 111870240 | A | 11/2020 |
| CN | 111973875 | A | 11/2020 |
| CN | 111990993 | A | 11/2020 |
| CN | 212038601 | U | 12/2020 |
| CN | 112402786 | A | 2/2021 |
| CN | 212789439 | U | 3/2021 |
| CN | 113041496 | A | 6/2021 |
| CN | 113599695 | A | 11/2021 |
| EP | 3562542 | | 11/2019 |
| IT | 201700000165 | A1 | 7/2018 |

OTHER PUBLICATIONS

First Office Action issued Mar. 2, 2024, for Application No. 202111093647.X and translation (16 pgs).

* cited by examiner

IMPLANTABLE MEDICAL LEAD

The present application claims priority to Chinese Patent Application No. 202111093647.X filed on Sep. 17, 2021, the disclosure of which is incorporated herein by reference in its entirety.

CROSS-REFERENCE TO RELATED APPLICATION(S)

This is a national stage application filed under 37 U.S.C. 371 based on International Patent Application No. PCT/CN2022/110914, filed Aug. 8, 2022, which claims priority to Chinese Patent Application No. 202111093647.X filed on Sep. 17, 2021, the disclosure of which is incorporated herein by reference in its entirety.

TECHNICAL FIELD

The present application relates to the field of medical devices and, in particular, to an implantable medical lead.

BACKGROUND

An implantable medical lead is implanted into the human body for applying electrical stimulation to a patient. In the existing art, one type of implantable medical lead uses a segmented ring stimulating ring. When a patient is given electrical stimulation, the stimulation signals are sent around 360 degrees. However, the nerve nuclei sites that need to be stimulated cannot be accurately located, and thus the symptom-free sites may receive unnecessary electrical stimulation, resulting in over-treatment in the brain sites that are not supposed to be targeted in the treatment and further causing unpredictable other symptoms such as slow movement, unsmooth speech, degeneration of swallowing function, and the like.

Another existing implantable medical lead includes a stimulation end, a connection end, and an intermediate conduction line portion located between the stimulation end and the connection end, where the stimulation end and the connection end are provided with segmented ring contacts, the intermediate conduction line portion is provided with helical metal guide wires, the contacts at the stimulation end are connected to the metal guide wires of the intermediate conduction line portion by welding, and the contacts at the connection end are connected to the metal guide wires of the intermediate conduction line portion by welding.

The method for connecting the contacts and the metal guide wires in the above implantable medical lead is relatively high in production cost and is relatively complicated in the production process, and when more stimulation contacts are required, more metal guide wires for conduction connection are required to be arranged. The above method is limited by the microtube diameter of the implantable medical lead and the size of the metal guide wire so it is very difficult or impossible to arrange more stimulation contacts (such as 18 stimulation contacts or 24 stimulation contacts), and the signals of an electric field around the stimulation contacts cannot be detected, which restricts the doctor's discrimination of the site of the disease, the theoretical research on more stimulation contact sites, and the flexibility of treatment. Therefore, it is urgent to invent an implantable medical lead that can accurately detect data of an electric field around the stimulation contacts.

SUMMARY

The object of the present application is to provide an implantable medical lead to solve the problem of difficulty in accurately detecting an electrical signal in a stimulation area of an implantable medical lead.

The object of the present application is achieved through the schemes below.

An implantable medical lead is provided. The implantable medical lead includes a conductive flexible circuit board. The conductive flexible circuit board is divided into a stimulation segment, a connection segment, and an intermediate segment located between the stimulation segment and the connection segment. An outer surface of the stimulation segment of the conductive flexible circuit board is provided with multiple stimulation contacts, and an outer surface of the connection segment of the conductive flexible circuit board is provided with multiple first connection contacts. Multiple stimulation contact conductive layers extending in a length direction of the conductive flexible circuit board are embedded in the conductive flexible circuit board, and each first connection contact is electrically connected to at least one stimulation contact through at least one stimulation contact conductive layer. The outer surface of the stimulation segment of the conductive flexible circuit board is provided with at least one collection contact each arranged near one of the multiple stimulation contacts and each insulated from the multiple stimulation contacts. The outer surface of the connection segment of the conductive flexible circuit board is provided with at least one second connection contact each insulated from the multiple first connection contacts. Multiple collection contact conductive layers extending in the length direction of the conductive flexible circuit board are embedded in the conductive flexible circuit board, the multiple collection contact conductive layers are insulated from the multiple stimulation contact conductive layers, and each second connection contact is electrically connected to at least one collection contact through at least one collection contact conductive layer.

In a possible implementation, the stimulation segment and the connection segment are each a cylindrical structure, and the intermediate segment is a cylindrical structure, a spiral structure or a structure formed by rolling a flattened wavy conductive flexible circuit board round.

In a possible implementation, the outer surface of the stimulation segment of the conductive flexible circuit board is provided with multiple collection contacts, at least one collection contact is provided near each stimulation contact, and each second connection contact is electrically connected to one collection contact through one collection contact conductive layer.

In a possible implementation, at least one collection contact is arranged within or around each stimulation contact.

In a possible implementation, each stimulation contact is at least one of a circle, an oval or a rectangle.

In a possible implementation, the conductive flexible circuit board includes: a flexible substrate; multiple first stimulation contact conductive layers, multiple second stimulation contact conductive layers, and multiple third stimulation contact conductive layers, where the multiple first stimulation contact conductive layers are arranged on the flexible substrate and located in the stimulation segment, the multiple second stimulation contact conductive layers are arranged on the flexible substrate and located in the intermediate segment, the multiple third stimulation contact conductive layers are arranged on the flexible substrate and located in the connection segment, and each second stimulation contact conductive layer is electrically connected to at least one first stimulation contact conductive layer and at least one third stimulation contact conductive layer; multiple first collection contact conductive layers, multiple second collection contact conductive layers, and multiple third collection contact conductive layers, where the multiple first collection contact conductive layers are arranged on the flexible substrate and located in the stimulation segment, the multiple second collection contact conductive layers are arranged on the flexible substrate and located in the intermediate segment, the multiple third collection contact conductive layers are arranged on the flexible substrate and located in the connection segment, and each second collection contact conductive layer is electrically connected to at least one first collection contact conductive layer and at least one third collection contact conductive layer; and an insulating layer, where the insulating layer is arranged on the flexible substrate and covers the multiple first stimulation contact conductive layers, the multiple second stimulation contact conductive layers, the multiple third stimulation contact conductive layers, the multiple first collection contact conductive layers, the multiple second collection contact conductive layers, and the multiple third collection contact conductive layers, a portion of the insulating layer in the stimulation segment is provided with multiple first openings and multiple third openings, each stimulation contact is electrically connected to one first stimulation contact conductive layer through one first opening, each collection contact is electrically connected to one first collection contact conductive layer through one third opening, a portion of the insulating layer in the connection segment is provided with multiple second openings and multiple fourth openings, each first connection contact is electrically connected to one third stimulation contact conductive layer through one second opening, and each second connection contact is electrically connected to one third collection contact conductive layer through one fourth opening.

In a possible implementation, each second stimulation contact conductive layer is electrically connected to and integrally formed with one first stimulation contact conductive layer and one third stimulation contact conductive layer; and/or each second collection contact conductive layer is electrically connected to and integrally formed with one first collection contact conductive layer and one third collection contact conductive layer.

In a possible implementation, in a thickness direction of the conductive flexible circuit board, the multiple stimulation contact conductive layers are distributed on at least two layers having different thicknesses of the conductive flexible circuit board, and at least a portion of at least two stimulation contact conductive layers overlaps in the thickness direction of the conductive flexible circuit board; and/or in the thickness direction of the conductive flexible circuit board, the multiple collection contact conductive layers are distributed on at least two layers having different thicknesses of the conductive flexible circuit board, and at least a portion of at least two collection contact conductive layers overlaps in the thickness direction of the conductive flexible circuit board.

In a possible implementation, each first connection contact is annular, the multiple annular first connection contacts and surrounds the outer surface of the connection segment in a circumferential direction of the connection segment, and the multiple first connection contacts are distributed at intervals; and/or each second connection contact is annular and surrounds the outer surface of the connection segment in the circumferential direction of the connection segment, and multiple second connection contacts are distributed at intervals.

Preferably, the implantable medical lead further includes: an inner liner, where the inner liner is arranged within the stimulation segment, the intermediate segment, and the connection segment of the conductive flexible circuit board; a first support tube and/or a second support tube, where the first support tube is arranged within the inner liner close to the stimulation segment to increase the rigidity of the stimulation segment of the implantable medical lead, and the second support tube is arranged within the inner liner close to the connection segment to increase the rigidity of the connection segment of the implantable medical lead; an outer sleeve, where the outer sleeve is arranged outside the intermediate segment of the conductive flexible circuit board and fits against the conductive flexible circuit board; and a locking ring, where the locking ring is fixedly sleeved on the outer sleeve corresponding to the intermediate segment and is adjacent to the connection segment of the implantable medical lead.

In a possible implementation, the implantable medical lead further includes a spherical crown, where the spherical crown has a first end and a second end that are opposite to each other, the first end of the spherical crown is arranged within the inner liner close to the stimulation segment, the second end of the spherical crown extends out from the inner liner, and the second end of the spherical crown has a smooth end surface.

Compared with the existing art, the effects of the present application at least include the following.

By arranging the collection contacts near the stimulation contacts, the cellular electrical signals in the electrically stimulated area of the implantable medical lead can be accurately detected. The nerve nuclei sites that need to be stimulated can be located through the cellular electrical signals collected by the collection contacts for proper treatment, thereby avoiding over-treatment in the brain sites due to unnecessary electrical stimulation of the symptom-free sites.

By embedding multiple conductive layers in the conductive flexible circuit board, electrically connecting each first connection contact to at least one stimulation contact through at least one conductive layer, and electrically connecting each second connection contact to at least one collection contact through at least one conductive layer, during the production of the conductive flexible circuit board into an implantable medical lead, since no wire needs to be arranged within the microtube diameter of the implantable medical lead, more conductive layers, stimulation contacts, and collection contacts can be arranged on the implantable medical lead, and the wire layout is more abundant and flexible, thereby achieving a wide application range.

BRIEF DESCRIPTION OF DRAWINGS

The present application is further described below in conjunction with drawings and embodiments.

REFERENCE LIST

Figure 1:
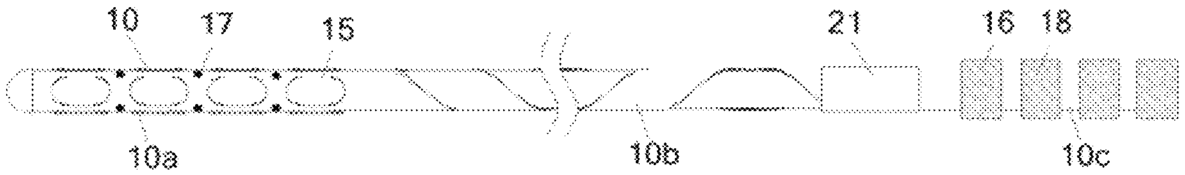
FIG. 1 is a structure view of an implantable medical lead with an outer sleeve omitted according to an embodiment of the present application.

10 conductive flexible circuit board
10*a* stimulation segment
10*b* intermediate segment
10*c* connection segment
11 flexible substrate
121 first stimulation contact conductive layer
122 third stimulation contact conductive layer
131 first collection contact conductive layer
132 third collection contact conductive layer
141 first opening
142 second opening
143 third opening
144 fourth opening
15 stimulation contact
16 first connection contact
17 collection contact
18 second connection contact
19 insulating layer
20 inner liner
21 locking ring
22 first support tube
23 second support tube
24 outer sleeve
25 spherical crown

DETAILED DESCRIPTION

The present application is further described below in conjunction with drawings and embodiments. It is to be noted that if not in collision, the embodiments or features described below may be combined with each other to form new embodiments.

The words expressing positions and orientations as used herein, such as "above" and "below", are illustrated with reference to the drawings, but modifications may be made as desired and are intended to be encompassed within the scope of the present application. The drawings of the present disclosure are used for illustrating only the relative positional relationship. The layer thicknesses of certain parts are shown exaggeratedly in the drawings to facilitate understanding. The layer thicknesses in the drawings do not represent the ratio of the actual layer thicknesses.

In the present application, "at least one" refers to one or more, and "multiple" refers to two or more. The term "and/or" describes the association relationships of associated objects and may indicate that three relationships may exist. For example, A and/or B may indicate three cases: A exists alone, A and B both exist, and B exists alone, where A and B may be singular or plural. The character "/" generally indicates that the associated objects are in an "or" relationship. "At least one of the following items" or similar expression refers to any combination of these items, including a single item or any combination of plural items. For example, at least one of a, b or c may be expressed as: a; b; c; a and b; a and c; b and c; or a, b, and c, where a, b, and c may be singular or plural. It is to be noted that "at least one" may also be interpreted as "one or more than one".

In the present application, the word "exemplary" or "for example" serves as an example, instance, or illustration. Any embodiment or design scheme described with "exemplary" or "for example" in the present application shall not be construed as being preferred or advantageous over other embodiments or design schemes. Specifically, the use of words such as "exemplary" or "for example" is intended to present relevant concepts in a specific manner.

One of the application fields (that is, implantable medical systems) of embodiments of the present application is briefly described below.

An implantable neurostimulation system (an implantable medical system) mainly includes a stimulator (that is, an implantable nerve stimulator) implanted inside the body of a patient and a program-controlled device arranged outside the body of the patient. Existing neuromodulation technology mainly involves the implantation of implantable medical leads in specific structures (that is, targets) in the body by means of stereotactic surgery and the delivery of electrical impulses from a stimulator implanted in the body of the patient to the targets by means of the implantable medical leads to regulate the electrical activities and functions of the corresponding neural structures and networks, thereby improving the symptoms and relieving the pain. The stimulator may be any one of an implantable electrical nerve stimulation device, an implantable cardiac electrical stimulation system (also known as a cardiac pacemaker), an implantable drug delivery system (IDDS) or a wire switch device. The implantable electrical nerve stimulation device is, for example, a deep brain stimulation (DBS) system, an implantable cortical nerve stimulation (CNS) system, an implantable spinal cord stimulation (SCS) system, an implantable sacral nerve stimulation (SNS) system, an implantable vagus nerve stimulation (VNS) system, and the like.

The stimulator may include an implantable pulse generator (IPG), an extension wire, and an implantable medical lead. The IPG is arranged in the body of a patient, receives program-controlled commands from a program-controlled device, supplies controllable electrical stimulation energy to the tissue in the body by means of sealed batteries and circuits, and delivers one or two paths of controllable electrical stimulation to specific areas of the tissue in the body by means of the implanted extension wire and implantable medical lead. The extension wire is used in conjunction with the IPG as a delivery medium for electrical stimulation signals and delivers the electrical stimulation signals generated by the IPG to the implantable medical lead.

In some possible implementations, the stimulated tissue in the body may be the brain tissue of the patient, and the stimulated sites may be specific parts of the brain tissue. The sites to be stimulated are generally different when the types of disease of patients vary. The type of applicable disease is not limited in the embodiments of the present application and may be diseases to which deep brain stimulation (DBS), spinal cord stimulation (SCS), pelvic stimulation, gastric stimulation, peripheral nerve stimulation, and functional electrical stimulation are applicable. The diseases that the DBS may be used to treat or manage include, but are not limited to: spasticity disorders (for example, epilepsy), pain, migraine, mental disorders (for example, major depressive disorder (MDD)), bipolar disorder, anxiety disorders, posttraumatic stress disorder, dysthymic disorder, obsessive-compulsive disorder (OCD), behavioral disorders, emotional disorders, memory disorders, mentation disorders, movement disorders (for example, essential tremor or Parkinson's disease), Huntington's disease, Alzheimer's disease, drug addictions, autism, or other neurological or psychiatric disorders and impairments.

In the embodiments of the present application, when the program-controlled device and the stimulator establish a program-controlled connection, the stimulation parameter of the stimulator may be adjusted by means of the program-controlled device (different stimulation parameters correspond to different electrical stimulation signals); or the stimulator may sense bioelectrical activities in the deep brain of the patient to collect electrophysiological signals, and the stimulation parameter of the electrical stimulation signal of the stimulator may be adjusted through the collected electrophysiological signals.

The stimulation parameter may include at least one of: a frequency (for example, the number of electrical stimulation pulse signals per unit time of 1 s, in Hz), a pulse width (the duration of each pulse, in μs), an amplitude (which is generally expressed in terms of a voltage and is the intensity of each pulse, in V), a timing (which, for example, may be consecutive or triggered), a stimulation mode (including one of a current mode, a voltage mode, a timing stimulation mode or a cyclic stimulation mode), upper and lower doctor-controlled limits (the range that can be adjusted by the doctor), or upper and lower patient-controlled limits (the range that can be independently adjusted by the patient).

In a specific application scenario, various stimulation parameters of the stimulator can be adjusted in a current mode or a voltage mode. The program-controlled device may be a doctor-program-controlled device (that is, a program-controlled device used by the doctor) or a patient-program-controlled device (that is, a program-controlled device used by the patient). The doctor-program-controlled device may be, for example, an intelligent terminal device such as a tablet computer, a laptop computer, a desktop computer and a mobile phone equipped with program-controlled software. The patient-program-controlled device may be, for example, an intelligent terminal device such as a tablet computer, a laptop computer, a desktop computer and a mobile phone equipped with program-controlled software and may also be other electronic devices having program-controlled functions (for example, a charger and a data collection device having program-controlled functions).

The data interaction between the doctor-program-controlled device and the stimulator is not limited in the embodiments of the present application, and when the doctor performs program control remotely, the doctor-program-controlled device may interact with the stimulator through a server and the patient-program-controlled device. When the doctor performs program control on the patient face to face, the doctor-program-controlled device may interact with the stimulator through the patient-program-controlled device, and the doctor-program-controlled device may also interact with the stimulator directly.

In some optional implementations, the patient-program-controlled device may include a host (which is in communication with the server) and a slave (which is in communication with the stimulator), and the host and the slave may be in communicable connection with each other. The doctor-program-controlled device may perform data interaction with the server via a 3G/4G/5G network, the server may perform data interaction with the host via a 3G/4G/5G network, the host may perform data interaction with the slave via a Bluetooth protocol/WIFI protocol/USB protocol, and the slave may perform data interaction with the stimulator via the operating frequency band of 401 MHz-406 MHz/operating frequency band of 2.4 GHz-2.48 GHz; the doctor-program-controlled device may also directly perform data interaction with the stimulator via the operating frequency band of 401 MHz-406 MHz/operating frequency band of 2.4 GHz-2.48 GHz.

Figure 2:
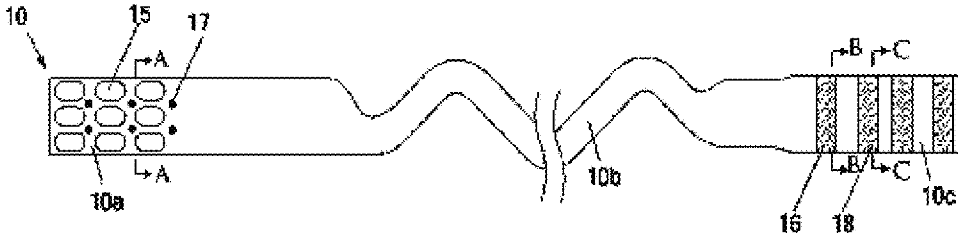
FIG. 2 is a structure view of an unrolled conductive flexible circuit board according to an embodiment of the present application.

With reference to FIGS. 1 and 2, FIG. 1 is a structure view of an implantable medical lead with an outer sleeve omitted according to an embodiment of the present application, and FIG. 2 is a structure view of an unrolled conductive flexible circuit board according to an embodiment of the present application.

The embodiments of the present application provide an implantable medical lead. The implantable medical lead includes a conductive flexible circuit board 10. The conductive flexible circuit board 10 is divided into a stimulation segment 10*a*, a connection segment 10*c*, and an intermediate segment 10*b* located between the stimulation segment 10*a* and the connection segment 10*c*. Before the conductive flexible circuit board 10 is made into an implantable medical lead, the conductive flexible circuit board 10 may be of a flattened structure, and during the production of the implantable medical lead, the conductive flexible circuit board 10 may be rolled round, where the stimulation segment 10*a* and the connection segment 10*c* are processed into a cylindrical structure, respectively, and the intermediate segment 10*b* is processed into a cylindrical structure, a spiral structure, or a structure formed by rolling a wavy conductive flexible circuit board round.

An outer surface of the stimulation segment 10*a* of the conductive flexible circuit board 10 is provided with multiple stimulation contacts 15, and an outer surface of the connection segment 10*c* of the conductive flexible circuit board 10 is provided with multiple first connection contacts 16. Multiple stimulation contact conductive layers extending in a length direction of the conductive flexible circuit board 10 are embedded in the conductive flexible circuit board 10, and each first connection contact 16 is electrically connected to at least one stimulation contact 15 through at least one stimulation contact conductive layer. The outer surface of the stimulation segment 10*a* of the conductive flexible circuit board 10 is provided with at least one collection contact 17, and the at least one collection contact 17 is each arranged near one of the multiple stimulation contacts 15 and each insulated from the multiple of stimulation contacts. In other words, the collection contacts 17 and the stimulation contacts 15 are insulated from each other, the multiple stimulation contacts 15 are preferably insulated from each other, and multiple collection contacts 17 are preferably insulated from each other. The outer surface of the connection segment 10*c* of the conductive flexible circuit board 10 is provided with at least one second connection contact 18, and the at least one second connection contact 18 is insulated from the multiple first connection contacts 16. In other words, the second connection contacts 18 and the first connection contacts 16 are insulated from each other, multiple second connection contacts 18 are preferably insulated from each other, and the multiple first connection contacts 16 are preferably insulated from each other. Multiple collection contact conductive layers extending in the length direction of the conductive flexible circuit board 10 are embedded in the conductive flexible circuit board 10, the multiple collection contact conductive layers are insulated from the multiple stimulation contact conductive layers, and each second connection contact 18 is electrically connected to at least one collection contact 17 through at least one collection contact conductive layer.

The stimulation contacts 15 arranged on the outer surface of the stimulation segment 10*a* can be used to perform electrical stimulation, and the electrically stimulated area of the implantable medical lead may be the lesion area to be treated. By arranging the collection contacts 17 near the stimulation contacts 15, the cellular electrical signals in the electrically stimulated area of the implantable medical lead can be accurately detected. The nerve nuclei sites that need to be stimulated can be located through the cellular electrical signals collected by the collection contacts 17 for proper treatment, thereby avoiding over-treatment in the brain sites due to unnecessary electrical stimulation of the symptom-free sites.

In addition, by embedding multiple stimulation contact conductive layers and multiple collection contact conductive layers in the conductive flexible circuit board 10, electrically connecting each first connection contact 16 to at least one stimulation contact 15 through at least one stimulation contact conductive layer, and electrically connecting each second connection contact 18 to at least one collection contact 17 through at least one collection contact conductive layer, since no wire needs to be arranged in the microtube diameter of the implantable medical lead, more conductive layers and contacts can be arranged on the implantable medical lead, and the wire layout is more abundant and flexible, thereby achieving a wide application range.

In some possible implementations, the outer surface of the stimulation segment 10*a* of the conductive flexible circuit board 10 is provided with multiple collection contacts 17, at least one collection contact 17 is provided near each stimulation contact 15, and each second connection contact 18 is electrically connected to one collection contact 17 through one collection contact conductive layer.

Figure 3:
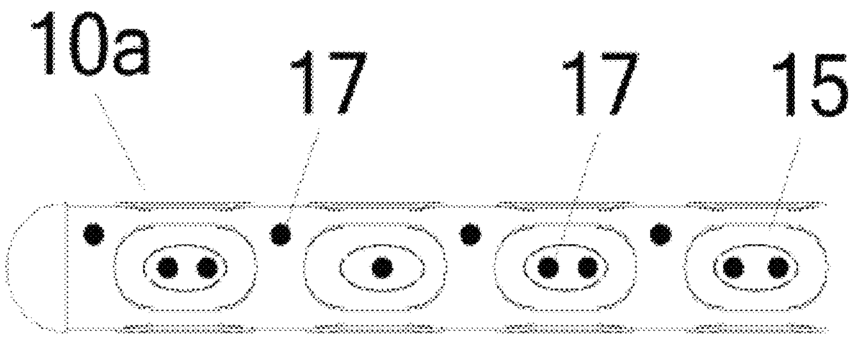
FIG. 3 is a structure view of a portion of an implantable medical lead adjacent to a stimulation segment according to an embodiment of the present application.

For the focal lesion area, multiple collection contacts 17 may be arranged near one stimulation contact 15, and the multiple collection contacts 17 may collect multiple cellular electrical signals from the same lesion area, thereby allowing the treatment of the focal lesion area to be more accurate. With reference to FIG. 3, FIG. 3 is a structure view of a portion of an implantable medical lead adjacent to a stimulation segment according to an embodiment of the present application. In some possible implementations, at least one collection contact 17 is arranged within or around each stimulation contact 15. Each stimulation contact 15 may be at least one of a circle, an oval or a rectangle.

When the collection contact 17 is arranged within the stimulation contact 15, the distance between the collection contact 17 and the stimulation contact 15 is very close, and the cellular electrical signals collected by the collection contact 17 can more accurately reflect the state of the electrically stimulated area.

Figure 4:
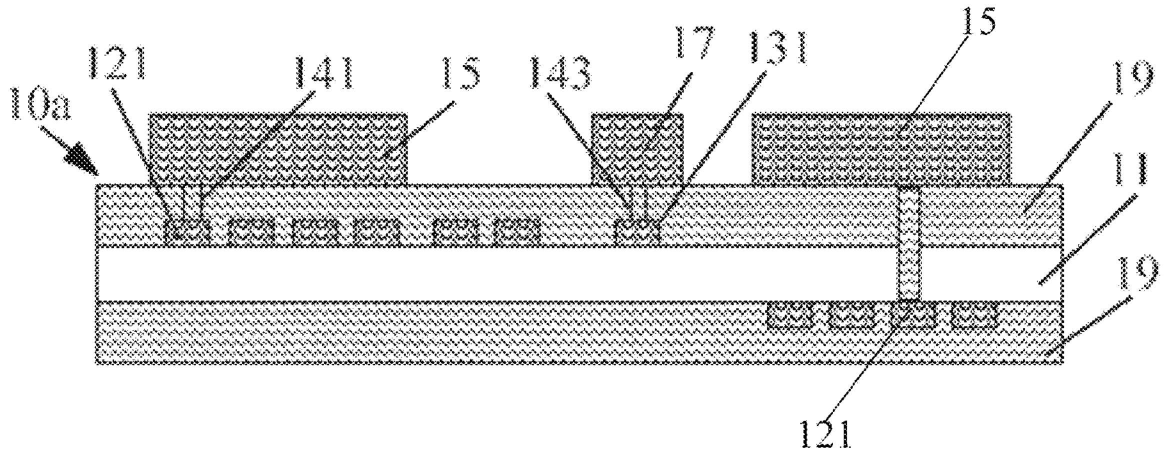
FIG. 4 is a partial section view taken along A-A in FIG. 2.
Figure 5:
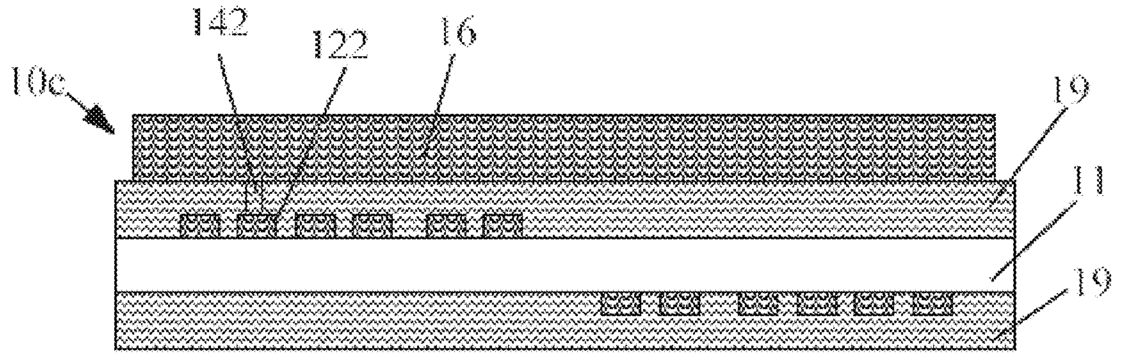
FIG. 5 is a section view taken along B-B in FIG. 2.
Figure 6:
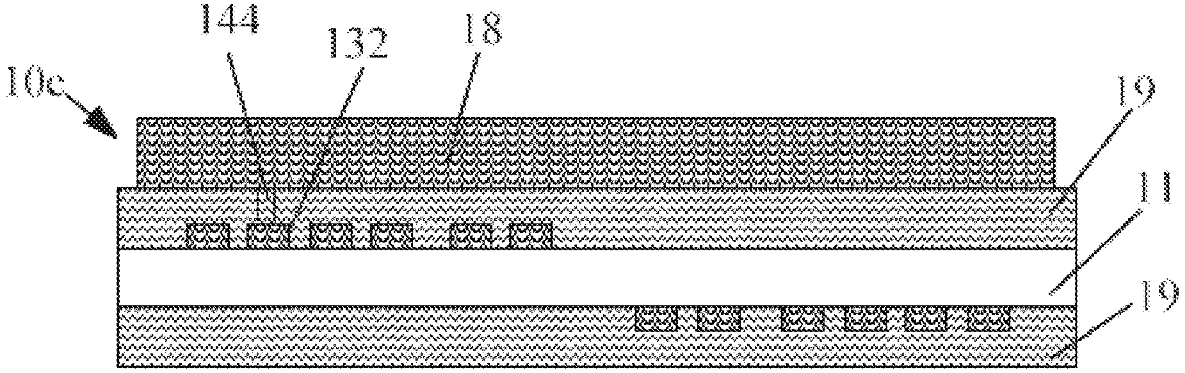
FIG. 6 is a section view taken along C-C in FIG. 2.

With reference to FIGS. 4, 5, and 6, FIG. 4 is a partial section view taken along A-A in FIG. 2, FIG. 5 is a section view taken along B-B in FIG. 2, and FIG. 6 is a section view taken along C-C in FIG. 2. In some possible implementations, the conductive flexible circuit board 10 includes a flexible substrate 11, multiple first stimulation contact conductive layers 121, multiple second stimulation contact conductive layers (not shown), multiple third stimulation contact conductive layers 122, multiple first collection contact conductive layers 131, multiple second collection contact conductive layers (not shown), multiple third collection contact conductive layers 132, and an insulating layer 19.

The multiple first stimulation contact conductive layers 121 are arranged on the flexible substrate 11 and located in the stimulation segment 10*a*, the multiple second stimulation contact conductive layers are arranged on the flexible substrate 11 and located in the intermediate segment 10*b*, the multiple third stimulation contact conductive layers 122 are arranged on the flexible substrate 11 and located in the connection segment 10*c*, and each second stimulation contact conductive layer is electrically connected to at least one first stimulation contact conductive layer 121 and at least one third stimulation contact conductive layer 122.

The multiple first collection contact conductive layers 131 are arranged on the flexible substrate 11 and located in the stimulation segment 10*a*, the multiple second collection contact conductive layers are arranged on the flexible substrate 11 and located in the intermediate segment 10*b*, the multiple third collection contact conductive layers 132 are arranged on the flexible substrate 11 and located in the connection segment 10*c*, and each second collection contact conductive layer is electrically connected to at least one first collection contact conductive layer 131 and at least one third collection contact conductive layer 132.

The insulating layer 19 is arranged on the flexible substrate 11 and covers the multiple first stimulation contact conductive layers 121, the multiple second stimulation contact conductive layers, the multiple third stimulation contact conductive layers 122, the multiple first collection contact conductive layers 131, the multiple second collection contact conductive layers, and the multiple third collection contact conductive layers 132. A portion of the insulating layer 19 in the stimulation segment 10*a* is provided with multiple first openings 141 and multiple third openings 143. Each stimulation contact 15 is electrically connected to one first stimulation contact conductive layer 121 through one first opening 141, and each collection contact 17 is electrically connected to one first collection contact conductive layer 131 through one third opening 143. A portion of the insulating layer 19 in the connection segment 10*c* is provided with multiple second openings 142 and multiple fourth openings 144. Each first connection contact 16 is electrically connected to one third stimulation contact conductive layer 122 through one second opening 142, and each second connection contact 18 is electrically connected to one third collection contact conductive layer 132 through one fourth opening 144.

The thickness of each first stimulation contact conductive layer 121, each second stimulation contact conductive layer, each third stimulation contact conductive layer 122, each first collection contact conductive layer 131, each second collection contact conductive layer, and each third collection contact conductive layer 132 may be any one of 0.01 mm, 0.02 mm or 0.03 mm, respectively. The thickness of each first stimulation contact conductive layer 121, each second stimulation contact conductive layer, each third stimulation contact conductive layer 122, each first collection contact conductive layer 131, each second collection contact conductive layer, and each third collection contact conductive layer 132 may be equal to each other, and with the equal thickness, the production process of the conductive layers can be simplified. The insulating layer 19 may be made of Parylene or other silicon-based materials.

As a result, by arranging multiple collection contact conductive layers and multiple stimulation contact conductive layers on the flexible substrate 11, the wire layout on the implantable medical lead is more abundant and flexible, thereby achieving a wide application range.

Specifically, each second stimulation contact conductive layer is electrically connected to one first stimulation contact conductive layer 121 and one third stimulation contact conductive layer 122, and each second stimulation contact conductive layer is integrally formed with the one first stimulation contact conductive layer 121 connected thereto and the one third stimulation contact conductive layer 122 connected thereto; and/or each second collection contact conductive layer is electrically connected to one first collection contact conductive layer 131 and one third collection contact conductive layer 132, and each second collection contact conductive layer is integrally formed with the one first collection contact conductive layer 131 connected thereto and the one third collection contact conductive layer 132 connected thereto.

As a result, one first connection contact 16 may be electrically connected to one stimulation contact 15 through one first stimulation contact conductive layer 121, one second stimulation contact conductive layer, and one third stimulation contact conductive layer 122, and one second connection contact 18 may be electrically connected to one collection contact 17 through one first collection contact conductive layer 131, one second collection contact conductive layer, and one third collection contact conductive layer 132. The above integrally formed structure may be achieved by arranging the multiple stimulation contact conductive layers and/or the multiple collection contact conductive layers in the same layer in the thickness direction of the flexible substrate 11. The above arrangement can simplify the production process and reduce the production difficulty.

In some possible implementations, in the thickness direction of the conductive flexible circuit board 10, the multiple stimulation contact conductive layers are distributed on at least two layers having different thicknesses of the conductive flexible circuit board 10, and at least a portion of at least two stimulation contact conductive layers overlaps in the thickness direction of the conductive flexible circuit board 10; and/or in the thickness direction of the conductive flexible circuit board 10, the multiple collection contact conductive layers are distributed on at least two layers having different thicknesses of the conductive flexible circuit board 10, and at least a portion of at least two collection contact conductive layers overlaps in the thickness direction of the conductive flexible circuit board 10.

As a result, the number of conductive layers can be increased with the width of the flexible substrate 11 unchanged. It is to be noted that in the thickness direction of the flexible substrate 11, the multiple first stimulation contact conductive layers 121 and/or the multiple first collection contact conductive layers 131 may be located in the same layer or in different layers, the multiple second stimulation contact conductive layers and/or the multiple second collection contact conductive layers may be located in the same layer or in different layers, and the multiple third stimulation contact conductive layers 122 and/or the multiple third collection contact conductive layers 132 may be located in the same layer or in different layers. When the conductive layers are located in the same layer, the production process can be simplified, and the production difficulty can be reduced; when the conductive layers are located in different layers, the number of conductive layers can be increased with the width of the flexible substrate 11 unchanged, thereby allowing an increase in the number of stimulation contacts 15.

In some possible implementations, each first connection contact 16 is annular and surrounds on the outer surface of the connection segment 10*c* in a circumferential direction of the connection segment 10*c*, and the multiple first connection contacts 16 are distributed at intervals; and/or each second connection contact 18 is annular and surrounds the outer surface of the connection segment 10*c* in a circumferential direction of the connection segment 10*c*, and multiple second connection contacts 18 are distributed at intervals. The width of each annular first connection contact 16 and/or each annular second connection contact 18 may be 0.8 mm, 1 mm or 1.5 mm.

When each first connection contact 16 and/or each second connection contact 18 are annular, instability of the electrical connection between the implantable medical lead and an external device due to the rotation of the implantable medical lead under the action of external force can be avoided.

Figure 7:
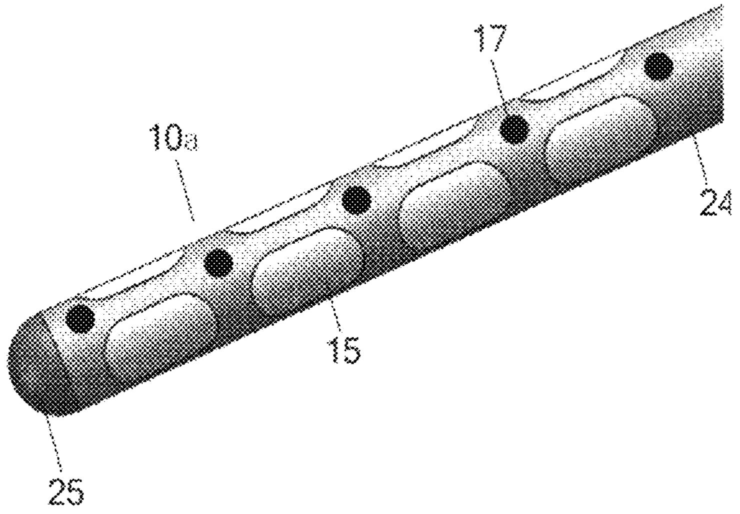
FIG. 7 is a structure view of a portion of another implantable medical lead adjacent to a stimulation segment according to an embodiment of the present application.
Figure 8:
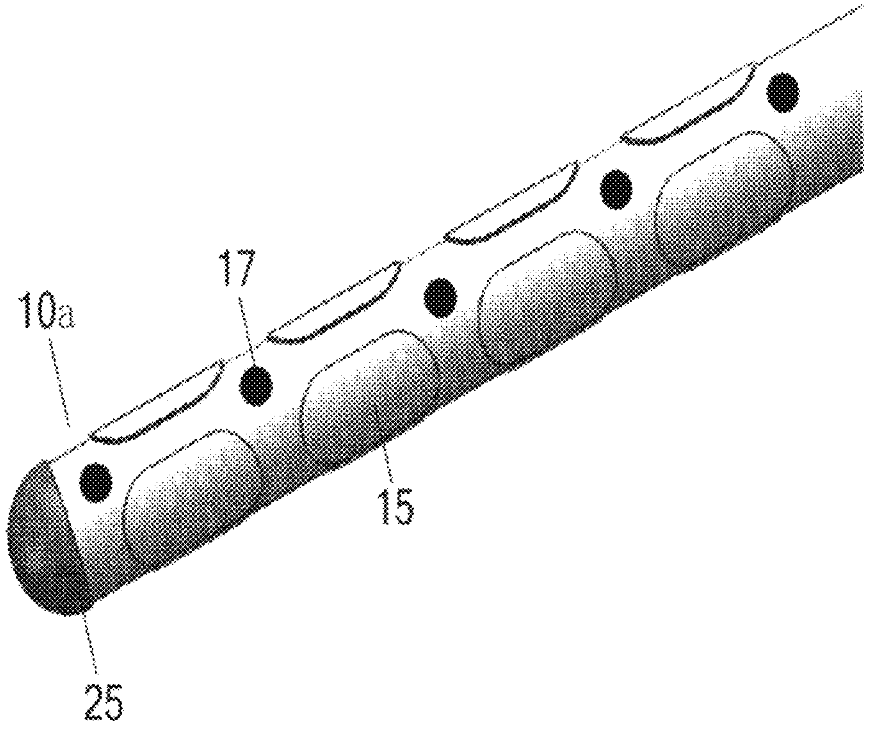
FIG. 8 is a structure view of the implantable medical lead of FIG. 7 with an outer sleeve omitted.
Figure 9:
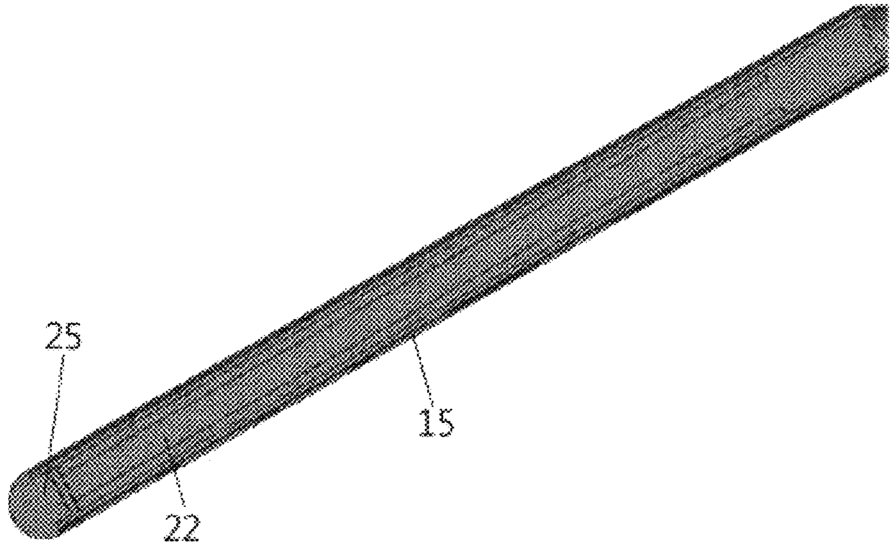
FIG. 9 is a partial section view of the implantable medical lead of FIG. 7.
Figure 10:
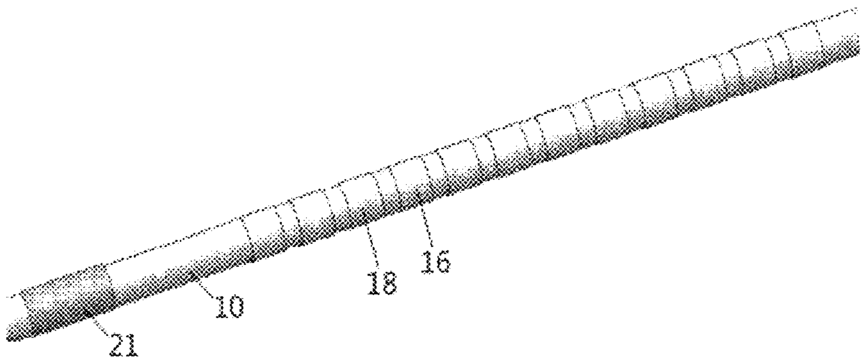
FIG. 10 is a structure view of a portion of an implantable medical lead adjacent to a connection segment according to an embodiment of the present application.
Figure 11:
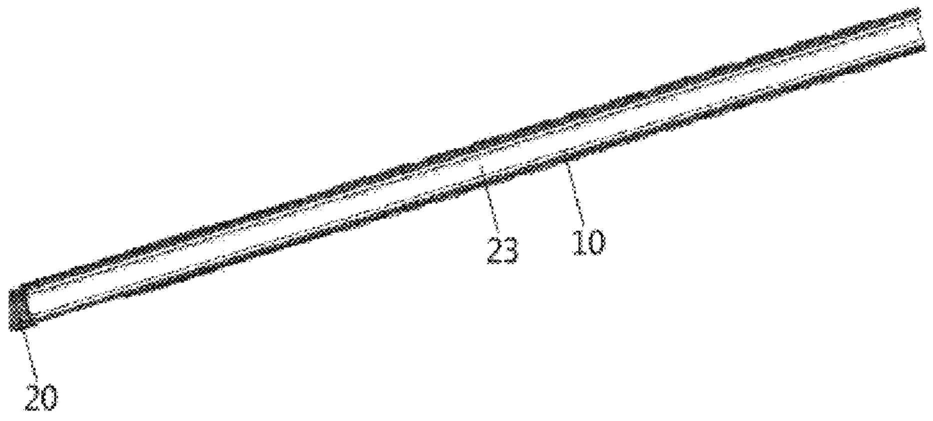
FIG. 11 is a partial section view of the implantable medical lead of FIG. 10.

With reference to FIGS. 7, 8, 9, 10, and 11, FIG. 7 is a structure view of a portion of another implantable medical lead adjacent to a stimulation segment according to an embodiment of the present application, FIG. 8 is a structure view of the implantable medical lead of FIG. 7 with an outer sleeve omitted, FIG. 9 is a partial section view of the implantable medical lead of FIG. 7, FIG. 10 is a structure view of a portion of an implantable medical lead adjacent to a connection segment according to an embodiment of the present application, and FIG. 11 is a partial section view of the implantable medical lead of FIG. 10.

In some possible implementations, the implantable medical lead may include an inner liner 20, an outer sleeve 24, a locking ring 21, and a first support tube 22 and/or a second support tube 23.

The inner liner 20 is arranged within the stimulation segment 10*a*, the intermediate segment 10*b*, and the connection segment 10*c* of the conductive flexible circuit board 10. The inner liner 20 may be made of a material that is not sensitive to thermal deformation, such as polyurethane. The inner liner 20 may have an outer diameter of 1.1 mm and an inner diameter of 0.9 mm. By arranging the inner liner 20, the rigidity of the implantable medical lead can be increased, thereby facilitating the implantation operation when the implantable medical lead is implanted.

The first support tube 22 is arranged within the inner liner 20 close to the stimulation segment 10*a* to increase the rigidity of the stimulation segment 10*a* of the implantable medical lead, and the second support tube 23 is arranged within the inner liner 20 close to the connection segment 10*c* to increase the rigidity of the connection segment 10*c* of the implantable medical lead. Although the stimulation segment 10*a* and the connection segment 10*c* are subjected to great pressure during the implantation of the implantable medical lead, the rigidity of the stimulation segment 10*a* and the connection segment 10*c* of the implantable medical lead is increased by means of the first support tube 22 and the second support tube 23, thereby improving the operation efficiency during the implantation and helping the doctor to complete the implantation operation. The first support tube 22 may have an outer diameter of 0.9 mm and an inner diameter of 0.52 mm, and the second support tube 23 may have an outer diameter of 0.9 mm and an inner diameter of 0.8 mm.

The outer sleeve 24 is arranged outside the intermediate segment 10*b* of the conductive flexible circuit board 10 and fits against the conductive flexible circuit board 10. The outer sleeve 24 may be made of polyurethane, and the outer sleeve 24 may have an outer diameter of 1.25 mm and an inner diameter of 1.17 mm. By arranging the outer sleeve 24, the conductive flexible circuit board 10 can be separated from the human tissue, thereby reducing possible adverse impacts of bodily fluids on the performance of the conductive flexible circuit board 10 and reducing possible adverse impacts of the conductive flexible circuit board 10 on the human tissue.

The locking ring 21 is fixedly sleeved on the outer sleeve 24 corresponding to the intermediate segment 10*b* and is adjacent to the connection segment 10*c* of the implantable medical lead. The length of the locking ring 21 may be 2.5 mm, and the distance between the locking ring 21 and the end surface of the connection segment 10*c* is, for example, 23.2 mm. The locking ring 21 may be a metal ring, and the locking ring 21 may be provided with a polydimethylsiloxane (PTFE) coating. The binding force between the locking ring 21 and the implantable medical lead preferably meets the condition that no release occurs under the drawing of 14 N. When the implantable medical lead is electrically connected to the stimulator (not shown) via a cable, the connection segment 10*c* of the implantable medical lead needs to be fixedly connected to one end of the cable. By arranging the locking ring 21, the connection segment 10*c* of the implantable medical lead is inserted into a connection member at one end of the cable and then may abut against the locking ring 21 through a fastener so that the implantable medical lead is fixedly connected to one end of the cable.

Specifically, the implantable medical lead further includes a spherical crown 25. The spherical crown 25 has a first end and a second end that are opposite to each other. The first end of the spherical crown 25 is arranged within the inner liner close to the stimulation segment, the second end of the spherical crown 25 extends out from the inner liner, and the second end of the spherical crown 25 has a smooth end surface. The spherical crown 25 may be made of a resin-type polymer material, the spherical crown 25 and the first support tube 22 may be formed into a seal structure, and the smooth end surface of the spherical crown 25 is, for example, a spherical crown nose. By setting the extension portion of the spherical crown 25 to be a smooth end surface, damage to the human tissue can be reduced when the implantable medical lead is implanted.

What is claimed is:

1. An implantable medical lead, comprising:

a conductive flexible circuit board, wherein the conductive flexible circuit board is divided into a stimulation segment, a connection segment, and an intermediate segment located between the stimulation segment and the connection segment;

wherein an outer surface of the stimulation segment of the conductive flexible circuit board is provided with a plurality of stimulation contacts, an outer surface of the connection segment of the conductive flexible circuit board is provided with a plurality of first connection contacts, a plurality of stimulation contact conductive layers extending in a length direction of the conductive flexible circuit board are embedded in the conductive flexible circuit board, and each of the plurality of the first connection contacts is electrically connected to at least one of the plurality of the stimulation contacts through at least one of the plurality of the stimulation contact conductive layers;

wherein the outer surface of the stimulation segment of the conductive flexible circuit board is provided with a collection contact arranged near one of the plurality of the stimulation contacts, wherein the collection contact and the plurality of the stimulation contacts are insulated, the outer surface of the connection segment of the conductive flexible circuit board is provided with a second connection contact insulated from the plurality of the first connection contacts, a plurality of collection contact conductive layers extending in the length direction of the conductive flexible circuit board are embedded in the conductive flexible circuit board, the plurality of the collection contact conductive layers are insulated from the plurality of the stimulation contact conductive layers, and the second connection contact is electrically connected to the collection contact through at least one of the plurality of the collection contact conductive layers;

wherein the conductive flexible circuit board comprises a flexible substrate and an insulating layer, the plurality of the stimulation contact conductive layers and the plurality of the collection contact conductive layers are arranged on the flexible substrate, the insulating layer covers the plurality of the stimulation contact conductive layers and the plurality of the collection contact conductive layers, and the insulating layer is provided with openings; and wherein connections between each of the plurality of the first connection contacts and the at least one of the plurality of the stimulation contact conductive layers, between the at least one of the plurality of the stimulation contacts and the at least one of the plurality of the stimulation contact conductive layers, between the second connection contact and the at least one of the plurality of the collection contact conductive layers, and between the collection contact and the at least one of the plurality of the collection contact conductive layers are all made through the openings.

2. The implantable medical lead according to claim 1, wherein the stimulation segment and the connection segment are each a cylindrical structure, and the intermediate segment is a cylindrical structure, a spiral structure, or a structure formed by rolling a flattened wavy conductive flexible circuit board round.

3. The implantable medical lead according to claim 1, wherein the outer surface of the stimulation segment of the conductive flexible circuit board is provided with a plurality of collection contacts, at least one of the plurality of the collection contacts is provided near each of the plurality of the stimulation contacts, and the second connection contact is electrically connected to one of the plurality of the collection contacts through one of the plurality of the collection contact conductive layers.

4. The implantable medical lead according to claim 1, wherein the collection contact is arranged within or around each of the plurality of the stimulation contacts.

5. The implantable medical lead according to claim 4, wherein the collection contact is arranged within each of the plurality of the stimulation contacts; an outer edge area of each of the plurality of the stimulation contacts is a stimulation area, and a center area of each of the plurality of the stimulation contacts is a collection area.

6. The implantable medical lead according to claim 1, wherein in a thickness direction of the conductive flexible circuit board, the plurality of the stimulation contact conductive layers are distributed on at least two layers having different thicknesses of the conductive flexible circuit board, and at least two stimulation contact conductive layers partially overlap in the thickness direction of the conductive flexible circuit board.

7. The implantable medical lead according to claim 6, wherein in the thickness direction of the conductive flexible circuit board, the plurality of the collection contact conductive layers are distributed on at least two layers having different thicknesses of the conductive flexible circuit board, and at least two collection contact conductive layers partially overlap in the thickness direction of the conductive flexible circuit board.

8. The implantable medical lead according to claim 1, wherein each of the plurality of the first connection contacts is annular and surrounds the outer surface of the connection segment in a circumferential direction of the connection segment, and the plurality of the first connection contacts are distributed at intervals.

9. The implantable medical lead according to claim 8, wherein the outer surface of the connection segment of the conductive flexible circuit board is provided with a plurality of second connection contacts; each of the plurality of the second connection contacts is annular and surrounds the outer surface of the connection segment in the circumferential direction of the connection segment, and the plurality of the second connection contacts are distributed at intervals.

10. The implantable medical lead according to claim 1, further comprising:

an inner liner, wherein the inner liner is arranged within the stimulation segment, the intermediate segment, and the connection segment of the conductive flexible circuit board;

a first support tube and a second support tube, wherein the first support tube is arranged within the inner liner close to the stimulation segment to increase rigidity of the stimulation segment of the implantable medical lead, and the second support tube is arranged within the inner liner close to the connection segment to increase rigidity of the connection segment of the implantable medical lead;

an outer sleeve, wherein the outer sleeve is arranged outside the intermediate segment of the conductive flexible circuit board and fits against the conductive flexible circuit board; and a locking ring, wherein the locking ring is fixedly sleeved on the outer sleeve corresponding to the intermediate segment and is adjacent to the connection segment of the implantable medical lead.

11. The implantable medical lead according to claim 10, further comprising a spherical crown, wherein the spherical crown has a first end and a second end that are opposite to each other, the first end of the spherical crown is arranged within the inner liner close to the stimulation segment, the second end of the spherical crown extends out from the inner liner, and the second end of the spherical crown has a smooth end surface.

12. The implantable medical lead according to claim 1, wherein in a thickness direction of the conductive flexible circuit board, the plurality of the collection contact conductive layers are distributed on at least two layers having different thicknesses of the conductive flexible circuit board, and at least two collection contact conductive layers partially overlap in the thickness direction of the conductive flexible circuit board.

13. The implantable medical lead according to claim 1, wherein the outer surface of the connection segment of the conductive flexible circuit board is provided with a plurality of second connection contacts; each of the plurality of the second connection contacts is annular and surrounds the outer surface of the connection segment in the circumferential direction of the connection segment, and the plurality of the second connection contacts are distributed at intervals.

14. The implantable medical lead according to claim 1, further comprising:

an inner liner, wherein the inner liner is arranged within the stimulation segment, the intermediate segment, and the connection segment of the conductive flexible circuit board;

a first support tube, wherein the first support tube is arranged within the inner liner close to the stimulation segment to increase rigidity of the stimulation segment of the implantable medical lead;

an outer sleeve, wherein the outer sleeve is arranged outside the intermediate segment of the conductive flexible circuit board and fits against the conductive flexible circuit board; and a locking ring, wherein the locking ring is fixedly sleeved on the outer sleeve corresponding to the intermediate segment and is adjacent to the connection segment of the implantable medical lead.

15. The implantable medical lead according to claim 1, further comprising:

an inner liner, wherein the inner liner is arranged within the stimulation segment, the intermediate segment, and the connection segment of the conductive flexible circuit board;

a second support tube, wherein the second support tube is arranged within the inner liner close to the connection segment to increase rigidity of the connection segment of the implantable medical lead;

an outer sleeve, wherein the outer sleeve is arranged outside the intermediate segment of the conductive flexible circuit board and fits against the conductive flexible circuit board; and a locking ring, wherein the locking ring is fixedly sleeved on the outer sleeve corresponding to the intermediate segment and is adjacent to the connection segment of the implantable medical lead.

16. The implantable medical lead according to claim 1, wherein at least three stimulation contacts are arranged at a same position of the stimulation segment in an axial direction of the stimulation segment, and are distributed at intervals along a circumferential direction of the stimulation segment.

* * * * *